United States Patent
Iwashita et al.

(10) Patent No.: US 11,047,808 B2
(45) Date of Patent: Jun. 29, 2021

(54) RADIATION IMAGING APPARATUS, RADIATION IMAGING SYSTEM, AND RADIATION IMAGING METHOD

(71) Applicant: CANON KABUSHIKI KAISHA, Tokyo (JP)

(72) Inventors: Atsushi Iwashita, Tokyo (JP); Kosuke Terui, Yokohama (JP); Katsuro Takenaka, Honjo (JP); Yoshiaki Ishii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 104 days.

(21) Appl. No.: 15/791,566

(22) Filed: Oct. 24, 2017

(65) Prior Publication Data

US 2018/0128755 A1     May 10, 2018

(30) Foreign Application Priority Data

Nov. 10, 2016  (JP) .............................. JP2016-219952

(51) Int. Cl.
*G01T 1/16*     (2006.01)
*G01N 23/04*    (2018.01)
(Continued)

(52) U.S. Cl.
CPC ........... *G01N 23/04* (2013.01); *A61B 6/4035* (2013.01); *A61B 6/4233* (2013.01);
(Continued)

(58) Field of Classification Search
CPC .... A61B 6/463; A61B 6/5229; H04N 5/3205; H04N 5/325
See application file for complete search history.

(56) References Cited

U.S. PATENT DOCUMENTS 5,886,353 A * 3/1999 Spivey ................ A61B 6/4233
                                                250/208.1
7,342,221 B2   3/2008 Takenaka et al.
(Continued)

FOREIGN PATENT DOCUMENTS

CN      1228163 A       9/1999
CN    101237819 A       8/2008
(Continued)

OTHER PUBLICATIONS

U.S. Appl. No. 15/563,148, filed Sep. 29, 2017, Kosuke Terui.
U.S. Appl. No. 15/564,946, filed Oct. 6, 2017, Kosuke Terui.

*Primary Examiner* — David P Porta
*Assistant Examiner* — Mamadou Faye
(74) *Attorney, Agent, or Firm* — Venable LLP

(57) ABSTRACT

A radiation imaging apparatus that obtains a radiation image by an energy subtraction method. Each pixel includes a conversion element that converts radiation into an electrical signal and a reset portion that resets the conversion element. Each pixel performs an operation of outputting a first signal corresponding to an electrical signal generated by the conversion element in a first period, and an operation of outputting a second signal corresponding to an electrical signal generated by the conversion element in the first period and a second period. Radiation having first energy is emitted in the first period, and radiation having second energy is emitted in the second period. In each pixel, the reset portion does not reset the conversion element during a period that includes the first period and the second period.

18 Claims, 8 Drawing Sheets

(51) Int. Cl.
 *H04N 5/32* (2006.01)
 *A61B 6/00* (2006.01)

(52) U.S. Cl.
 CPC .......... *A61B 6/4291* (2013.01); *A61B 6/4441* (2013.01); *A61B 6/481* (2013.01); *A61B 6/482* (2013.01); *A61B 6/5264* (2013.01); *A61B 6/542* (2013.01); *H04N 5/32* (2013.01); *H04N 5/3205* (2013.01)

(56) References Cited

U.S. PATENT DOCUMENTS

| | | | |
|---|---|---|---|
| 7,343,000 B2 | 3/2008 | Kameshima et al. |
| 7,381,963 B2 | 6/2008 | Endo et al. |
| 7,386,089 B2 | 6/2008 | Endo et al. |
| 7,403,594 B2 | 7/2008 | Endo et al. |
| 7,442,939 B2 | 10/2008 | Yagi et al. |
| 7,514,663 B2 | 4/2009 | Yagi et al. |
| 7,532,706 B2 | 5/2009 | Kameshima et al. |
| 7,541,591 B2 | 6/2009 | Endo et al. |
| 7,573,038 B2 | 8/2009 | Yokoyama et al. |
| 7,613,277 B2 | 11/2009 | Takenaka et al. |
| 7,683,337 B2 | 3/2010 | Takenaka et al. |
| 7,718,973 B2 | 5/2010 | Endo et al. |
| 7,724,874 B2 | 5/2010 | Kameshima et al. |
| 7,732,776 B2 | 6/2010 | Takenaka et al. |
| 7,750,309 B2 | 7/2010 | Endo et al. |
| 7,791,034 B2 | 9/2010 | Kameshima et al. |
| 7,791,035 B2 | 9/2010 | Yokoyama et al. |
| 7,847,263 B2 | 12/2010 | Yagi et al. |
| 7,869,568 B2 | 1/2011 | Yokoyama et al. |
| 7,872,218 B2 | 1/2011 | Endo et al. |
| 7,880,145 B2 | 2/2011 | Yagi et al. |
| 8,093,562 B2 | 1/2012 | Yokoyama et al. |
| 8,107,588 B2 | 1/2012 | Kameshima et al. |
| 8,167,486 B2 | 5/2012 | Takenaka et al. |
| 8,222,611 B2 | 7/2012 | Yagi et al. |
| 8,247,779 B2 | 8/2012 | Kameshima et al. |
| 8,576,294 B2 | 11/2013 | Kameshima et al. |
| 8,723,996 B2 | 5/2014 | Yokoyama et al. |
| 8,792,024 B2 | 7/2014 | Takenaka et al. |
| 8,809,795 B2 | 8/2014 | Takenaka et al. |
| 8,829,438 B2 | 9/2014 | Sato et al. |
| 9,048,154 B2 | 6/2015 | Takenaka et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,270,907 B2 | 2/2016 | Naito et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,737,271 B2 | 8/2017 | Iwashita et al. |
| 9,812,474 B2 | 11/2017 | Yagi et al. |
| 2002/0024601 A1 | 2/2002 | Kaifu et al. |
| 2002/0190215 A1* | 12/2002 | Tashiro ............. H01L 27/14658 250/370.11 |
| 2003/0086523 A1 | 5/2003 | Tashiro et al. |
| 2008/0232549 A1 | 9/2008 | Poorter |
| 2010/0148080 A1 | 6/2010 | Endo et al. |
| 2011/0317054 A1 | 12/2011 | Kameshima et al. |
| 2012/0087471 A1 | 4/2012 | Naito et al. |
| 2014/0112448 A1 | 4/2014 | Takenaka et al. |
| 2014/0239186 A1 | 8/2014 | Sato et al. |
| 2014/0361189 A1 | 12/2014 | Kameshima et al. |
| 2015/0293238 A1 | 10/2015 | Iwashita |
| 2016/0084969 A1 | 3/2016 | Sato et al. |
| 2016/0116612 A1* | 4/2016 | Lee ........................ G01T 1/24 378/62 |
| 2016/0178764 A1 | 6/2016 | Ryu et al. |
| 2016/0270755 A1 | 9/2016 | Takenaka et al. |
| 2016/0363674 A1* | 12/2016 | Jacob ...................... G01T 1/247 |
| 2016/0373672 A1* | 12/2016 | Liu ........................ G01T 1/247 |
| 2017/0285189 A1 | 10/2017 | Ryu et al. |

FOREIGN PATENT DOCUMENTS

| | | |
|---|---|---|
| CN | 102547148 A | 7/2012 |
| JP | 2009-504221 | 2/2009 |
| JP | 2014-090960 A | 5/2014 |
| KR | 10-2008-0042806 A | 5/2008 |
| KR | 10-2016-0047314 A | 5/2016 |
| WO | WO 2007/017773 A2 | 2/2007 |

\* cited by examiner

RADIATION IMAGING APPARATUS, RADIATION IMAGING SYSTEM, AND RADIATION IMAGING METHOD

BACKGROUND OF THE INVENTION

Field of the Invention

The present invention relates to a radiation imaging apparatus, a radiation imaging system, and a radiation imaging method.

Description of the Related Art

There is an energy subtraction method as an imaging method that applies a radiation imaging apparatus. The energy subtraction method is a method of obtaining new images (for example, a bone image and a soft tissue image) by processing a plurality of images obtained by capturing an object a plurality of times while changing energy of radiation to irradiate the object. A time interval during which a plurality of radiation images are captured is, for example, several seconds or more in a radiation imaging apparatus to capture a still image, about 100 msec in a general radiation imaging apparatus for a moving image, and about 10 msec even in a radiation imaging apparatus for a high-speed moving image. If the object moves in this time interval, an artifact is caused by that movement. It is therefore difficult to obtain, by the energy subtraction method, a radiation image of an object such as a heart that moves fast.

Japanese Patent Laid-Open No. 2009-504221 describes a system that performs dual energy imaging. In this system, the tube voltage of an X-ray source is set to the first kV value, and then changed to the second kV value in imaging. Then, the first signal corresponding to the first sub-image is integrated when the tube voltage is the first kV value, and integration is reset after the integrated signal is transferred to a sample and hold node. Subsequently, the second signal corresponding to the second sub-image is integrated when the tube voltage is the second kV value. Consequently, readout of the integrated first signal and integration of the second signal are performed parallelly.

A method described in Japanese Patent Laid-Open No. 2009-504221 performs readout of the integrated first signal and integration of the second signal parallelly, making it possible to shorten a time interval during which two images for the energy subtraction method are captured. In the method described in Japanese Patent Laid-Open No. 2009-504221, however, a reset operation exists after integration and transfer of the first signal corresponding to the first sub-image in order to obtain two radiation images (the first sub-image and the second sub-image). When a radiation irradiation time is shortened up to about 1 msec in order to suppress the influence of an object movement, the object is irradiated with radiation wastefully for a time at 10 percent of the radiation irradiation time even if the reset operation can be completed in 0.1 msec.

SUMMARY OF THE INVENTION

The present invention provides a technique advantageous in obtaining a radiation image for an energy subtraction method in a shorter time while reducing radiation irradiation that does not contribute to imaging.

One of the aspects of the present invention provides a radiation imaging apparatus that obtains a radiation image by an energy subtraction method of obtaining a new image by processing a plurality of images obtained by capturing an object a plurality of times while changing energy of radiation to irradiate the object, the apparatus comprising: a pixel array that includes a plurality of pixels, wherein each of the plurality of pixels includes a conversion element that converts radiation into an electrical signal and a reset portion that resets the conversion element, each of the plurality of pixels performs an operation of outputting a first signal corresponding to an electrical signal generated by the conversion element in a first period, and an operation of outputting a second signal corresponding to an electrical signal generated by the conversion element in the first period and a second period different from the first period, radiation having first energy is emitted in the first period, and radiation having second energy is emitted in the second period, and the radiation imaging apparatus has a mode in which, in each of the plurality of pixels, the reset portion does not reset the conversion element during a period that includes the first period and the second period.

Further features of the present invention will become apparent from the following description of exemplary embodiments with reference to the attached drawings.

DESCRIPTION OF THE EMBODIMENTS

An exemplary embodiment of the present invention will be described below with reference to the accompanying drawings.

Figure 1:
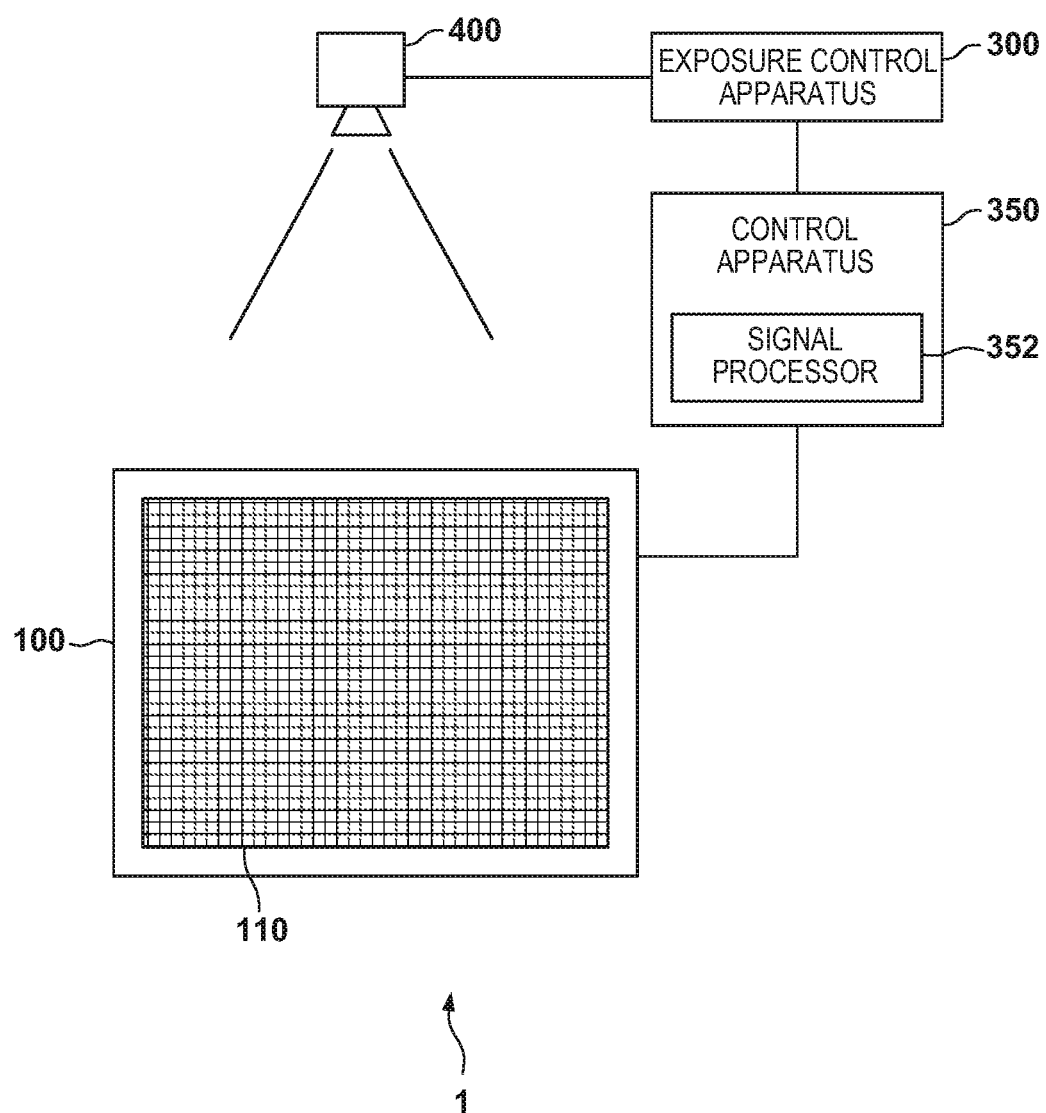
FIG. 1 is a view showing the arrangement a radiation imaging system according to an embodiment of the present invention.

FIG. 1 shows the arrangement of a radiation imaging system 1 according to an embodiment of the present invention. The radiation imaging system 1 includes a radiation imaging apparatus 100. The radiation imaging system 1 or the radiation imaging apparatus 100 is a system or apparatus for obtaining a radiation image by an energy subtraction method. The energy subtraction method is a method of obtaining new images (for example, a bone image and a soft tissue image) by processing a plurality of images obtained by capturing an object a plurality of times while changing energy of radiation to irradiate the object. The term radiation can include, for example, α-rays, β-rays, γ-rays, particle rays, and cosmic rays in addition to X-rays.

The radiation imaging system 1 can include a radiation source 400 that generates radiation, an exposure control apparatus 300 that controls the radiation source 400, and a control apparatus 350 that controls the exposure control apparatus 300 (radiation source 400) and the radiation imaging apparatus 100. The control apparatus 350 can include a signal processor 352 that processes a signal supplied from the radiation imaging apparatus 100. All or some functions of the control apparatus 350 can be incorporated in the radiation imaging apparatus 100. Alternatively, some functions of the radiation imaging apparatus 100 can be incorporated in the control apparatus 350. The control apparatus 350 can be formed by a computer (processor) and a memory that stores programs provided for the computer. The signal processor 352 can be made of some of the programs. Alternatively, the signal processor 352 can be mode of a computer (processor) and a memory that stores programs provided for the computer. The control apparatus 350 may be formed by a DSP (digital signal processor) or a PLA (programmable logic array) entirely or partially. The control apparatus 350 and the signal processor 352 may be designed and manufactured by a logic synthesis tool based on a file that describes their operations.

The exposure control apparatus 300 can include, for example, an exposure switch and in response to the fact that the exposure switch is turned on, cause the radiation source 400 to emit radiation and notify the control apparatus 350 of information indicating a timing at which the radiation is emitted. Alternatively, the exposure control apparatus 300 causes the radiation source 400 to emit radiation in accordance with a command from the control apparatus 350.

The radiation source 400 has a function of changing radiation energy (wavelength). The radiation source 400 can change the radiation energy by, for example, changing a tube voltage (a voltage applied between the cathode and anode of the radiation source 400). The radiation source 400 can emit radiation having a plurality of different kinds of energies.

The radiation imaging apparatus 100 includes a pixel array 110 that includes a plurality of pixels. Each of the plurality of pixels includes a convertor that converts radiation into an electrical signal (for example, charges) and a reset portion that resets the convertor. Each pixel may be configured to convert the radiation into the electrical signal directly or may be configured to convert the radiation into light such as visible light, and then convert the light into the electrical signal. In the latter case, a scintillator for converting radiation into light can be used. The plurality of pixels that form the pixel array 110 can share the scintillator.

Figure 2:
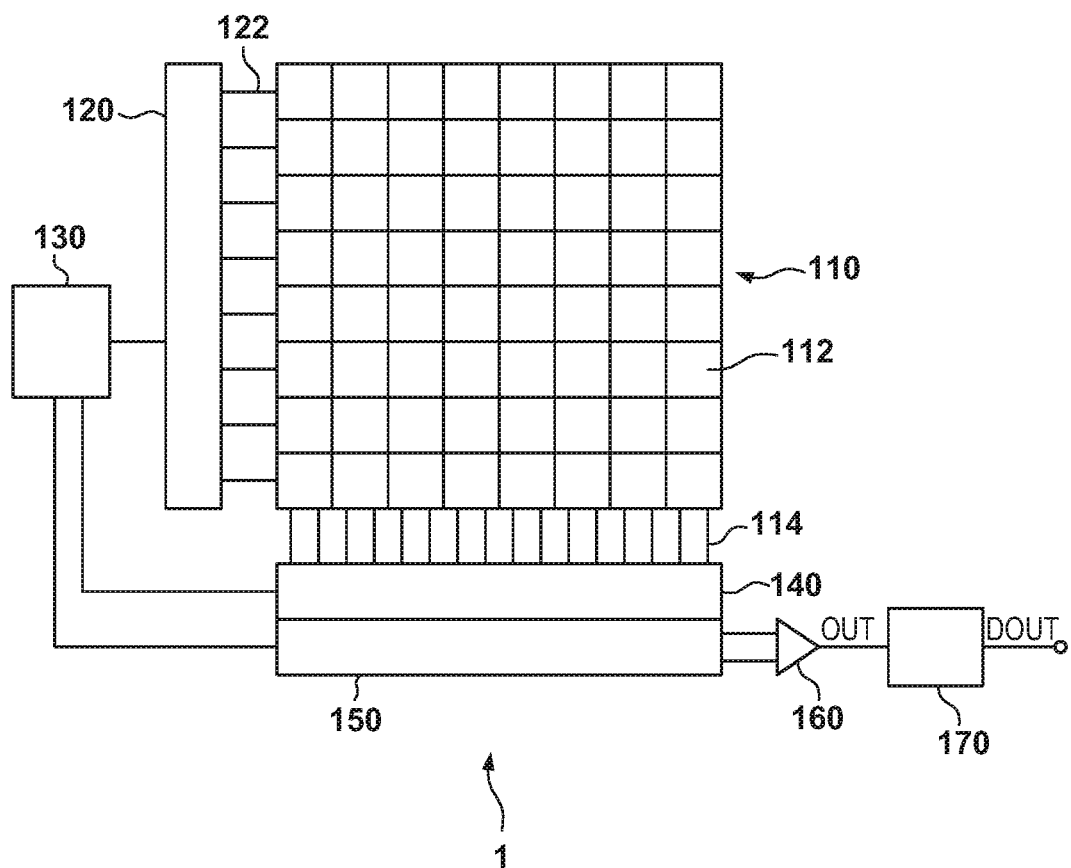
FIG. 2 is a view showing an example of the arrangement of a radiation imaging apparatus.

FIG. 2 shows an example of the arrangement of the radiation imaging apparatus 100. As described above, the radiation imaging apparatus 100 includes the pixel array 110 that includes a plurality of pixels 112. The plurality of pixels 112 can be arrayed so as to form a plurality of rows and a plurality of columns. The radiation imaging apparatus 100 can additionally include a row selection circuit 120 that selects the rows of the pixel array 110. The row selection circuit 120 selects the rows by driving row control signals 122.

The radiation imaging apparatus 100 can also include a readout circuit 140 that reads out signals from the pixels 112 of the row selected by the row selection circuit 120 out of the plurality of rows of the pixel array 110. The readout circuit 140 reads out signals for the plurality of columns output to a plurality of column signal transmission paths 114 of the pixel array 110. The column signal transmission path 114 of each column can include, for example, a plurality of column signal lines that transmit a plurality of signals detected by the pixels 112. For example, the noise levels of the pixels 112 and radiation signals corresponding to radiation detected by the pixels 112 can be output to the plurality of column signal lines. The readout circuit 140 can be configured to read out the noise levels and the radiation signals, respectively, output to the column signal transmission paths 114.

The radiation imaging apparatus 100 can include a column selection circuit 150 that selects, in a predetermined order, signals for the plurality of columns read out from the pixels of the rows of the pixel array 110 selected by the readout circuit 140. The radiation imaging apparatus 100 can also include an amplifier unit 160 that amplifies the signals selected by the column selection circuit 150. Note that when the readout circuit 140 reads out a pair of the noise level and radiation signal from each pixel 112, the amplifier unit 160 may be configured as a differential amplifier that amplifies a difference between the radiation signal and the noise level forming the pair or may be configured to amplify them individually. The radiation imaging apparatus 100 can further include an A/D convertor 170 that A/D-converts a signal OUT output from the amplifier unit 160 and outputs a digital signal DOUT (radiation image signal).

The radiation imaging apparatus 100 can include a timing generator (can also be referred to as a controller or a state machine) 130 that controls the row selection circuit 120, the readout circuit 140, the column selection circuit 150, and the amplifier unit 160.

Figure 3:
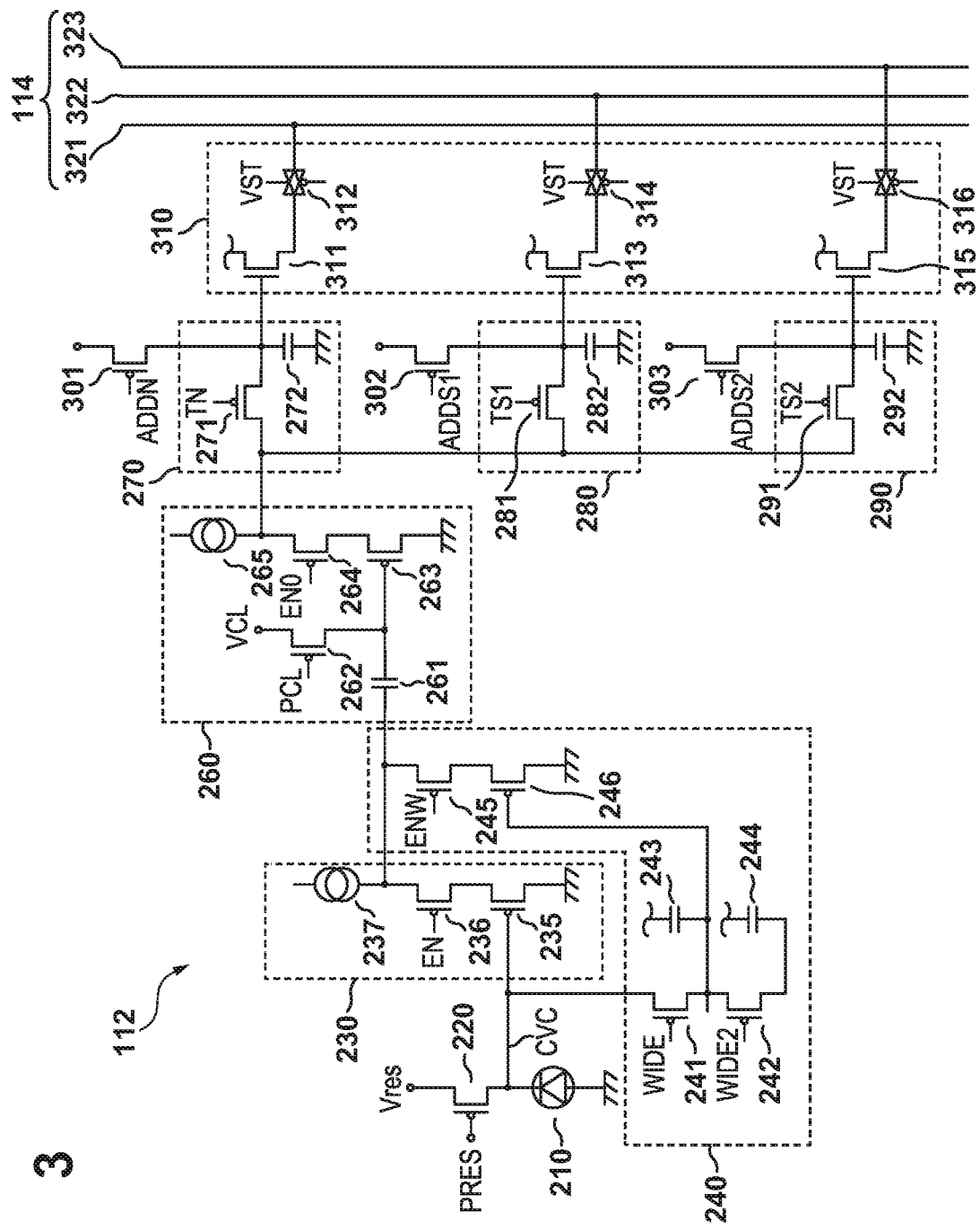
FIG. 3 is a circuit diagram showing an example of the arrangement of a pixel.

FIG. 3 shows an example of the arrangement of one pixel 112. The pixel 112 includes, for example, a conversion element 210, a reset switch 220 (reset portion), an amplifier circuit 230, a sensitivity changing portion 240, a clamp circuit 260, sample and hold circuits (holding portions) 270, 280, and 290, and an output circuit 310.

The conversion element 210 converts radiation into an electrical signal. The conversion element 210 can be formed by, for example, a scintillator that can be shared by the plurality of pixels and a photoelectric conversion element. The conversion element 210 includes a charge accumulation portion that accumulates a converted electrical signal (charges), that is, an electrical signal corresponding to radiation. The charge accumulation portion is connected to the input terminal of the amplifier circuit 230.

The amplifier circuit 230 can include MOS transistors 235 and 236, and a current source 237. The MOS transistor 235 is connected to the current source 237 via the MOS transistor 236. The MOS transistor 235 and the current source 237 form a source follower circuit. The MOS transistor 236 is an enable switch which is turned on by activating an enable signal EN, and sets the source follower circuit formed by the MOS transistor 235 and the current source 237 in an operation state.

The charge accumulation portion of the conversion element 210 and the gate of the MOS transistor 235 function as a charge-voltage convertor CVC that converts charges accumulated in the charge accumulation portion into a voltage. That is, a voltage $V$ (=$Q/C$) determined by charges $Q$ accumulated in the charge accumulation portion and a capacitance value $C$ of the charge-voltage convertor appears in the charge-voltage convertor CVC. The charge-voltage convertor CVC is connected to a reset potential Vres via the reset switch 220. When a reset signal PRES is activated, the reset switch 220 is turned on, and the potential of the charge-voltage convertor is reset to the reset potential Vres. The reset switch 220 can include a transistor that has the first main electrode (drain) connected to the charge accumulation portion of the conversion element 210, the second main electrode (source) to which the reset potential Vres is applied, and a control electrode (gate). The transistor electrically connects the first main electrode and the second main electrode by receiving an ON voltage at the control electrode, and resets the charge accumulation portion of the conversion element 210.

The clamp circuit 260 clamps, by a clamp capacitor 261, a reset noise level output from the amplifier circuit 230 in accordance with the potential of the reset charge-voltage convertor CVC. The clamp circuit 260 is a circuit configured to cancel the reset noise level from a signal (radiation signal) output from the amplifier circuit 230 in accordance with charges (electrical signal) converted by the conversion element 210. The reset noise level includes kTC noise at the time of reset of the charge-voltage convertor CVC. A clamp operation is performed by turning on a MOS transistor 262 by activating a clamp signal PCL, and then turning off the MOS transistor 262 by deactivating the clamp signal PCL.

The output side of the clamp capacitor 261 is connected to the gate of a MOS transistor 263. The source of the MOS transistor 263 is connected to a current source 265 via a MOS transistor 264. The MOS transistor 263 and the current source 265 form a source follower circuit. The MOS transistor 264 is an enable switch which is turned on by activating an enable signal EN0 supplied to its gate, and sets the source follower circuit formed by the MOS transistor 263 and the current source 265 in an operation state.

The output circuit 310 includes MOS transistors 311, 313, and 315 and row selection switches 312, 314, and 316. The MOS transistors 311, 313, and 315, respectively, form source follower circuits with current sources (not shown) connected to column signal lines 321, 322, and 323.

The sample and hold circuit 280 (the first holding portion or the first signal holding portion) can sample and hold (hold) a radiation signal (first signal) as a signal output from the clamp circuit 260 in accordance with charges generated in the conversion element 210. The sample and hold circuit 280 can include a switch 281 and a capacitor 282. The switch 281 is turned on by activating a sample and hold signal TS1. The radiation signal (first signal) output from the clamp circuit 260 is written in the capacitor 282 via the switch 281 by activating the sample and hold signal TS1.

In the example shown in FIG. 3, the pixel 112 can include the additional sample and hold circuit 290 (second holding portion) configured to write a radiation signal. The sample and hold circuit 290 can sample and hold (hold) a radiation signal (second signal) as a signal output from the clamp circuit 260 in accordance with charges generated in the conversion element 210. The sample and hold circuit 290 can include a switch 291 and a capacitor 292. The switch 291 is turned on by activating a sample and hold signal TS2. The radiation signal (second signal) output from the clamp circuit 260 is written in the capacitor 292 via the switch 291 by activating the sample and hold signal TS2. The pixel 112 may further include an additional sample and hold circuit configured to write a radiation signal. That is, the pixel 112 can include a plurality (the arbitrary number) of sample and hold circuits (holding portions) configured to write radiation signals.

In a state in which the reset switch 220 resets the potential of the charge-voltage convertor CVC, and the MOS transistor 262 is turned on, the clamp circuit 260 outputs the noise level (offset component) of the clamp circuit 260. The sample and hold circuit 270 (second signal holding portion) can sample and hold (hold) the noise level of the clamp circuit 260. The sample and hold circuit 270 can include a switch 271 and a capacitor 272. The switch 271 is turned on by activating a sample and hold signal TN. A noise level output from the clamp circuit 260 is written in the capacitor 272 via the switch 271 by activating the sample and hold signal TN. In this embodiment, the sample and hold circuit 270 (second signal holding portion) can also be used to hold a radiation signal as a signal output from the clamp circuit 260 in accordance with charges generated in the conversion element 210.

When row selection signals VST are activated, signals corresponding to signals held by the sample and hold circuits 270, 280, and 290 are output to the column signal lines 321, 322, and 323 that form the column signal transmission paths 114. More specifically, a signal N corresponding to a signal (a noise level or a radiation signal) held by the sample and hold circuit 270 is output to the column signal line 321 via the MOS transistor 311 and the row selection switch 312. A signal S1 corresponding to a signal (first radiation signal) held by the sample and hold circuit 280 is output to the column signal line 322 via the MOS transistor 313 and the row selection switch 314. A signal S2 corresponding to a signal (second radiation signal) held by the sample and hold circuit 290 is output to the column signal line 323 via the MOS transistor 315 and the row selection switch 316.

The pixel 112 may include addition switches 301, 302, and 303 configured to add signals of the plurality of pixels 112. In an addition mode, addition mode signals ADDN, ADDS1, and ADDS2 are activated. The capacitors 272 of the plurality of pixels 112 are connected to each other by activating the addition mode signal ADDN, averaging signals (noise levels). The capacitors 282 of the plurality of pixels 112 are connected to each other by activating the addition mode signal ADDS1, averaging signals. The capacitors 292 of the plurality of pixels 112 are connected to each other by activating the addition mode signal ADDS2, averaging signals.

The pixel 112 can include the sensitivity changing portion 240. The sensitivity changing portion 240 can include switches 241 and 242, capacitors 243 and 244, and MOS transistors 245 and 246. When a first change signal WIDE is activated, the switch 241 is turned on, and the capacitance value of the first additional capacitor 243 is added to the capacitance value of the charge-voltage convertor CVC. Consequently, the sensitivity of the pixel 112 is decreased. Further, when a second change signal WIDE 2 is also activated, the switch 242 is also turned on, and the capacitance value of the second additional capacitor 244 is added to the capacitance value of the charge-voltage convertor CVC. Consequently, the sensitivity of the pixel 112 is further decreased. A dynamic range can be widened by adding a function of decreasing the sensitivity of the pixel 112. An enable signal ENW may be activated when the first change signal WIDE is activated. In this case, the MOS transistor 246 performs a source follower operation. Note that when the switch 241 of the sensitivity changing portion 240 is turned on, the potential of the charge accumulation portion of the conversion element 210 may be changed by charge redistribution. Consequently, some signals may be destructed.

The above-described reset signal Pres, enable signal EN, clamp signal PCL, enable signal EN0, sample and hold signals TN, TS1, and TS2, and row selection signals VST are control signals controlled by the row selection circuit 120 and correspond to the row control signals 122 of FIG. 2.

Figure 4:
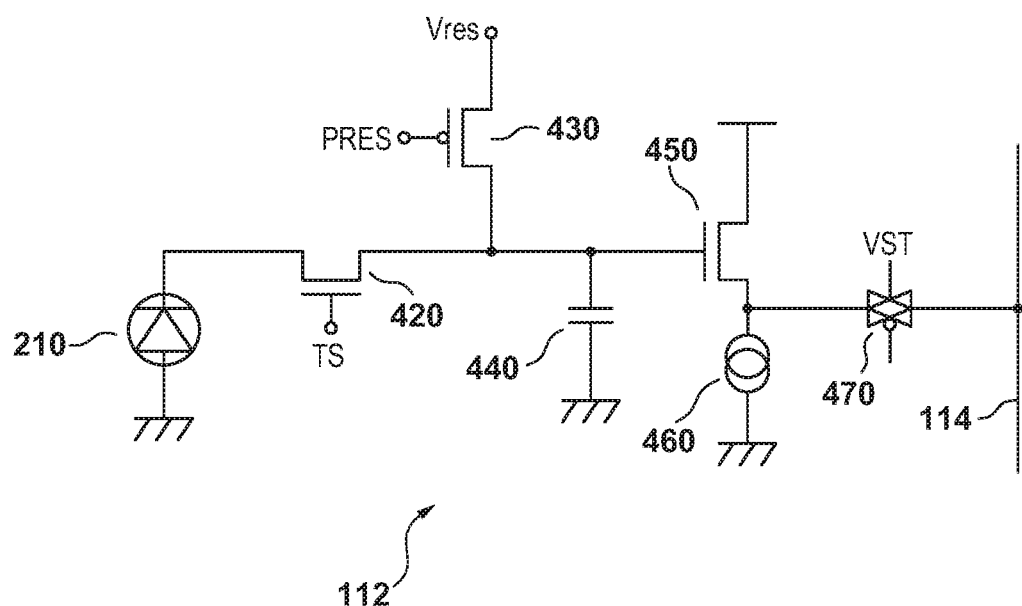
FIG. 4 is a circuit diagram showing another example of the arrangement of the pixel.

FIG. 4 shows another example of the arrangement of the pixel 112. In the example shown in FIG. 4, the pixel 112 includes the conversion element 210, a switch 420, a reset switch 430, a capacitor 440, a MOS transistor 450, a current source 460, and a row selection switch 470. The conversion element 210 can have the same arrangement as the aforementioned conversion element 210. The switch 420 writes (that is, samples and holds), in the capacitor 440, charges accumulated in the charge accumulation portion of the conversion element 210 by activating a sample and hold signal TS driven by the row selection circuit 120. The MOS transistor 450 forms a source follower circuit with the current source 460. The row selection switch 470 activates the row selection signals VST driven by the row selection circuit 120. When the row selection switch 470 is turned on, the MOS transistor 450 outputs, to the column signal transmission path 114, a signal corresponding to a signal held by the capacitor 440. Note that in the arrangement shown in FIG. 4, the potential of the charge accumulation portion of the conversion element 210 may be changed by charge injection when the switch 420 is turned on. Consequently, some signals may be destructed.

On the other hand, in the pixel 112 having the arrangement as shown in FIG. 3, signals are not destructed in, for example, the charge accumulation portion of the conversion element 210 in a sample and hold operation. That is, in the pixel 112 having the arrangement as shown in FIG. 3, the radiation signals can be nondestructively read out. Such an arrangement is advantageous to radiation imaging to which the energy subtraction method is applied to be described below and is particularly advantageous to the third to sixth modes to be described below. Therefore, an example will be described below in which the pixel 112 has the arrangement shown in FIG. 3.

The radiation imaging apparatus 100 and a radiation imaging method using this of this embodiment can have a plurality of modes for obtaining radiation images by the energy subtraction method. These modes will be described below.

Figure 5:
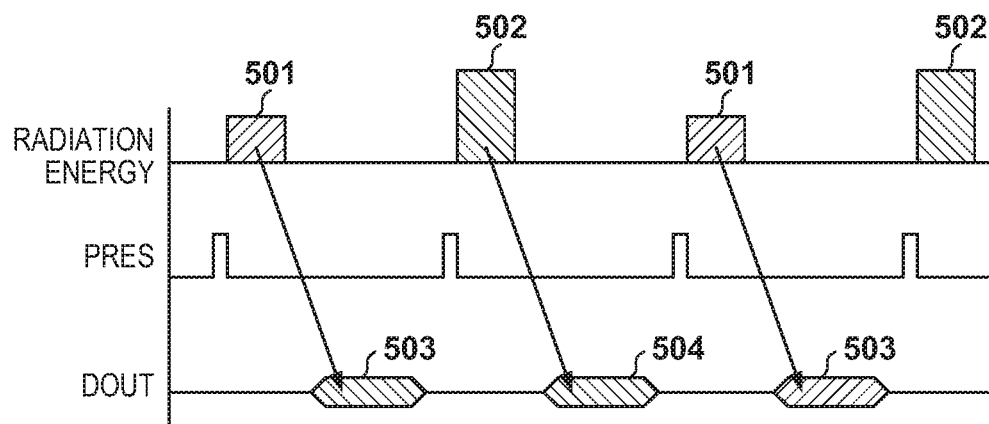
FIG. 5 is a timing chart showing an operation in the first mode.

FIG. 5 shows the operation of the radiation imaging apparatus 100 or radiation imaging system 1 in the first mode. In FIG. 5, the abscissa indicates a time. "Radiation energy" is energy of radiation which is emitted from the radiation source 400 and irradiates the radiation imaging apparatus 100. "PRES" is the reset signal PRES. "DOUT" is an output of the A/D convertor 170. The control apparatus 350 can control synchronization of radiation emission from the radiation source 400 and the operation of the radiation imaging apparatus 100. The timing generator 130 controls an operation in the radiation imaging apparatus 100. The clamp signal PCL is also activated over a predetermined period in a period during which the reset signal PRES is activated, and the clamp circuit 260 clamps a noise level.

The conversion element 210 is reset by activating the reset signal PRES over a predetermined period, and then radiation 501 having the first energy is emitted. Subsequently, charges (electrical signal) accumulated in each pixel 112 of the pixel array 110 by the radiation 501 are output as radiation signals 503 from the radiation imaging apparatus 100.

Subsequently, the conversion element 210 is reset by activating the reset signal PRES over the predetermined period, and then the radiation 501 having the second energy different from the first energy is emitted. Subsequently, charges (electrical signal) accumulated in each pixel 112 of the pixel array 110 by irradiation with radiation 502 are output from the radiation imaging apparatus 100 as a radiation signal 504. The signal processor 352 of the control apparatus 350 obtains a subtraction image by processing the radiation signals 503 and 504 in accordance with the energy subtraction method.

In the first mode, reset, irradiation with the radiation 501 of the first energy, output of the radiation signals 503 corresponding to it, reset, irradiation with the radiation 502 of the second energy, and output of the radiation signal 504 corresponding to it are performed sequentially. Therefore, the first mode is disadvantageous to radiation imaging of fast-moving object but is advantageous in capturing a still object accurately because it can obtain a radiation image of the first energy and a radiation image of the second energy while separating them completely.

Note that various methods can be adopted as the energy subtraction method. For example, it is possible, by calculating a difference between the radiation image of the first energy and the radiation image of the second energy, to obtain a bone image and a soft tissue image. The bone image and the soft tissue image may be generated by solving nonlinear simultaneous equations based on the radiation image of the first energy and the radiation image of the second energy. It is also possible to obtain a contrast medium image and the soft tissue image based on the radiation image of the first energy and the radiation image of the second energy. It is also possible to obtain an electron density image and an effective atomic number image based on the radiation image of the first energy and the radiation image of the second energy.

Figure 6:
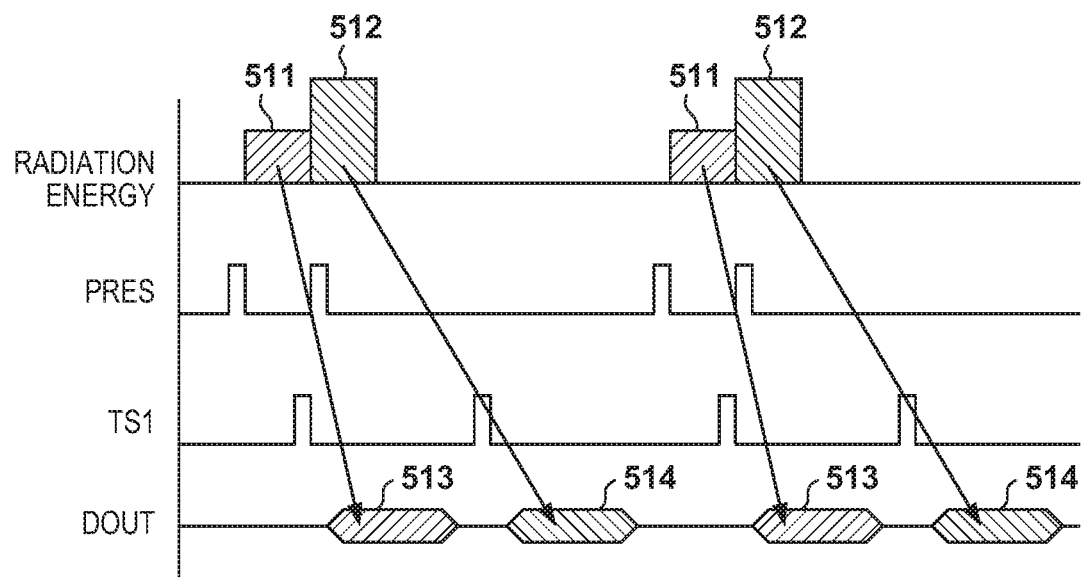
FIG. 6 is a timing chart showing an operation in the second mode.

FIG. 6 shows the operation of the radiation imaging apparatus 100 or radiation imaging system 1 in the second mode. In FIG. 6, the abscissa indicates a time. "Radiation energy" is energy of radiation which is emitted from the radiation source 400 and irradiates the radiation imaging apparatus 100. "PRES" is the reset signal PRES. "TS1" is the sample and hold signal TS1. "DOUT" is an output of the A/D convertor 170. The control apparatus 350 can control synchronization of radiation emission from the radiation source 400 and the operation of the radiation imaging apparatus 100. The timing generator 130 controls an operation in the radiation imaging apparatus 100. The clamp signal PCL is also activated over a predetermined period in a period during which the reset signal PRES is activated, and the clamp circuit 260 clamps a noise level.

The conversion element 210 is reset by activating the reset signal PRES over a predetermined period, and then radiation 511 having the first energy and radiation 512 having the second energy different from the first energy are emitted. Note that the radiation 511 and the radiation 512 may be emitted successively in terms of time or with a time interval between them.

The irradiation times of the radiations 511 and 512 are preset, and a sample and hold operation performed by the sample and hold circuit 280 in accordance with the sample and hold signal TS1 ends immediately before irradiation with the radiation 512. Subsequently, the conversion element 210 is reset by activating the reset signal PRES over the predetermined period. Note that in accordance with the sample and hold signal TS1, the sample and hold circuit 280 samples and holds a radiation signal generated by irradiation with the radiation 511 having the first energy.

Signals sampled and held by the sample and hold circuit 280 in accordance with the sample and hold signal TS1 are output as radiation signals 513 from the radiation imaging apparatus 100. Subsequently, the sample and hold circuit 280 performs the sample and hold operation in accordance with the sample and hold signal TS1. Consequently, the sample and hold circuit 280 samples and holds radiation signals generated by irradiation with the radiation 512 having the second energy. Signals sampled and held by the sample and hold circuit 280 in accordance with the sample and hold signal TS1 are output as radiation signals 514 from the radiation imaging apparatus 100. The signal processor 352 of the control apparatus 350 obtains a subtraction image by processing the radiation signals 513 and the radiation signals 514 in accordance with the energy subtraction method.

In the second mode, irradiation with the radiation 512 of the second energy is started before the output of the radiation signals 513 ends. Therefore, the second mode is superior to the first mode in radiation imaging of the fast-moving object. However, reset is performed in a period that includes a period during which the radiation 511 of the first energy is emitted and a period during which the radiation 512 of the second energy is emitted. Thus, information on radiation emitted in a reset period is lost by that reset. Consequently, image quality may deteriorate accordingly.

The third to sixth modes to be described below are superior to the first mode and the second mode in radiation imaging of the fast-moving object. In the third to sixth modes, each pixel 112 performs an operation of outputting the first signal corresponding to an electrical signal generated by the conversion element 210 in a first period T1 and an operation of outputting the second signal corresponding to an electrical signal generated by the conversion element 210 in a second period T2. Note that the second period T2 is different from the first period T1. Radiation having the first energy is emitted in the first period T1, and radiation having the second energy is emitted in the second period T2. In each of the plurality of pixels 112, during the period that includes the first period T1 and the second period T2, the reset switch 220 (reset portion) does not reset the conversion element 210 (the reset signal Pres (voltage thereof) does not change). Hence, radiation information is never lost by reset during the period that includes the first period T1 and the second period T2. This is advantageous in obtaining a more accurate radiation image by the energy subtraction method while reducing wasteful radiation irradiation.

Note that in a case in which radiation having the third energy is emitted in addition to the radiation having the first and second energies, a third period T3 can be provided in addition to the first period T1 and the second period T2, and the radiation having the third energy can be emitted in the third period. In this case, in each of the plurality of pixels 112, during a period that includes the first period T1, the second period T2, and the third period, the reset switch 220 (reset portion) does not reset the conversion element 210. The first to third energies can be different from each other. It is only necessary, however, that at least two of them are different from each other.

Moreover, in a case in which radiation having the fourth energy is emitted in addition to the radiation having the first to third energies, a fourth period T4 can be provided in addition to the first period T1, the second period T2, and the third period T3, and the radiation having the fourth energy can be emitted in the fourth period. In this case, in each of the plurality of pixels 112, during a period that includes the first period T1, the second period T2, the third period T3, and the fourth period, the reset switch 220 (reset portion) does not reset the conversion element 210. The first to fourth energies can be different from each other. It is only necessary, however, that at least two of them are different from each other.

Figure 7:
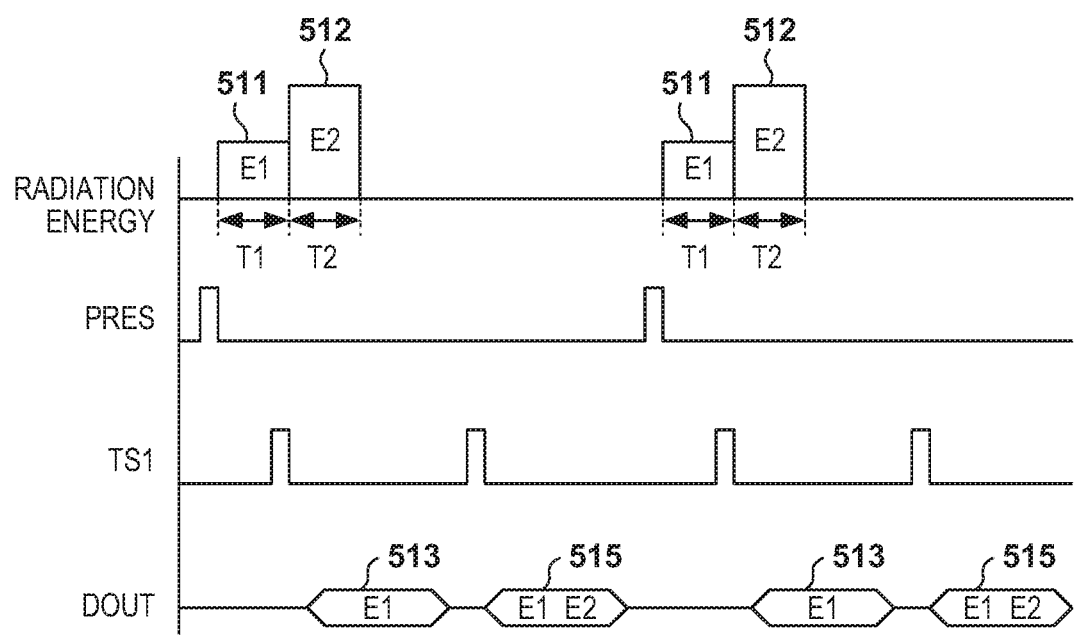
FIG. 7 is a timing chart showing an operation in the third mode.

The third to sixth modes will be described below more specifically. FIG. 7 shows the operation of the radiation imaging apparatus 100 or radiation imaging system 1 in the third mode. In FIG. 7, the abscissa indicates a time. "Radiation energy" is energy of radiation which is emitted from the radiation source 400 and irradiates the radiation imaging apparatus 100. "PRES" is the reset signal PRES. "TS1" is the sample and hold signal TS1. "DOUT" is an output of the A/D convertor 170. The control apparatus 350 can control synchronization of radiation emission from the radiation source 400 and the operation of the radiation imaging apparatus 100. The timing generator 130 controls an operation in the radiation imaging apparatus 100. The clamp signal PCL is also activated over a predetermined period in a period during which the reset signal PRES is activated, and the clamp circuit 260 clamps a noise level.

The conversion element 210 is reset by activating the reset signal PRES over a predetermined period, and then the radiation 511 having first energy E1 and the radiation 512 having second energy E2 different from the first energy E1 are emitted. Note that the radiation 511 and the radiation 512 may be emitted successively in terms of time or with a time interval between them.

The irradiation times of the radiations 511 and 512 are preset, and a sample and hold operation performed by the sample and hold circuit 280 in accordance with the sample and hold signal TS1 ends immediately before irradiation with the radiation 512. Note that in accordance with the sample and hold signal TS1, the sample and hold circuit 280 samples and holds a signal generated by irradiation with the radiation 511 having the first energy E1.

Unlike the second mode, reset according to the end of a sample and hold operation in the first period T1 is not performed in the third mode. In other words, in the third mode, reset is not performed in the period that includes the first period T1 and the second period T2. Therefore, charges (electrical signal) generated by irradiation with the radiation 511 of the first energy E1 remain in the charge accumulation portion of the conversion element 210.

Signals sampled and held by the sample and hold circuit 280 in accordance with the sample and hold signal TS1 are output, from the radiation imaging apparatus 100, as the radiation signals 513 corresponding to irradiation with the radiation 511 of the first energy E1.

Subsequently to irradiation with the radiation 511 of the first energy E1 in the first period T1, irradiation with the radiation 512 of the second energy E2 is performed in the second period T2. Consequently, in addition to charges generated by irradiation with the radiation of the first energy E1 in the first period T1, charges generated by irradiation with the radiation of the second energy E2 in the second period T2 are accumulated in the charge accumulation portion of the conversion element 210. The clamp circuit 260 outputs a radiation signal corresponding to the charges accumulated in the conversion element 210.

When the output of the radiation signals 513 ends, the sample and hold circuit 280 performs a sample and hold operation in accordance with the sample and hold signal TS1. Consequently, the sample and hold circuit 280 samples and holds radiation signals corresponding to the charges generated by irradiation with the radiation 511 of the first energy E1 in the first period T1 and charges generated by irradiation with the radiation 512 of the second energy E2 in the second period T2. Subsequently, the signals sampled and held by the sample and hold circuit 280 are output as radiation signals 515 from the radiation imaging apparatus 100.

The signal processor 352 of the control apparatus 350 obtains a subtraction image by processing the radiation signals 513 and the radiation signals 515 in accordance with the energy subtraction method. Note that the signal processor 352 can obtain, by subtracting the value of each radiation signal 513 from the value of a corresponding one of the radiation signals 515, a radiation image generated by irradiation with the radiation 512 of the second energy E2. That is, as in the first mode and second mode, a radiation image generated by irradiation with the radiation of the first energy and a radiation image generated by irradiation with the radiation of the second energy can also be obtained in the third mode. The subtraction image can be obtained by processing these radiation images in accordance with the energy subtraction method.

In the third mode, reset is not performed in the period that includes the first period T1 and the second period T2, and thus the radiation information is never lost by reset. Furthermore, in the third mode, irradiation with the radiation 512 of the second energy is started before the output of the radiation signals 513 ends as in the second mode. Therefore, the third mode is superior to the first mode in radiation imaging of the fast-moving object.

Note that in the third mode, a radiation signal corresponding to the sum of the charges generated by the radiation 511 of the first energy E1 and the charges generated by irradiation with the radiation 512 of the second energy E2 needs to be read out. As described above, in the arrangement shown in FIG. 4, the potential of the charge accumulation portion of the conversion element may be changed by charge injection when the charges generated by the radiation 511 of the first energy E1 are read out, destructing some signals. It is therefore preferable, in order to execute the third mode, to adopt a pixel capable of nondestructively reading out charges (signal) generated in the photoelectric convertor (charge accumulation portion) as in the arrangement shown in FIG. 3.

Even with the arrangement shown in FIG. 3, the potential of the charge accumulation portion of the conversion element may be changed by charge distribution in driving to change sensitivity, destructing some signals. It is therefore preferable, in order to execute the third mode, to adopt driving not to change sensitivity. From the above, it can be said that the charges of the charge accumulation portion are not preferably destructed in order to execute the third mode. More specifically, the arrangement, as exemplified in FIG. 3, with one or more transistors each having the first main electrode which is connected to the charge accumulation portion, the second main electrode which is not connected to the charge accumulation portion, and a control electrode will be considered. In such an arrangement, it is preferable that a voltage applied to the control electrode of the one or more transistor is not changed during the period that includes the first period T1 and the second period T2. However, in an application capable of allowing destruction of some signals, driving to change sensitivity can also be adopted in the arrangements shown in FIGS. 3 and 4.

As described above, the clamp signal PCL can also be activated over the predetermined period in the period during which the reset signal PRES is activated, and the clamp circuit 260 clamps the noise level, and then the sample and hold circuit 270 can sample and hold this noise level. In the first to third modes, when a signal is read out from each pixel 112, a radiation signal can be read out from the sample and hold circuit 280 (first signal holding portion), and a noise level can be read out from the sample and hold circuit 270 (second signal holding portion). The amplifier unit 160 can perform differential amplification on a pair of the radiation signal and noise level thus read out. That is, a difference between the radiation signal and the noise level can be amplified.

Figure 8:
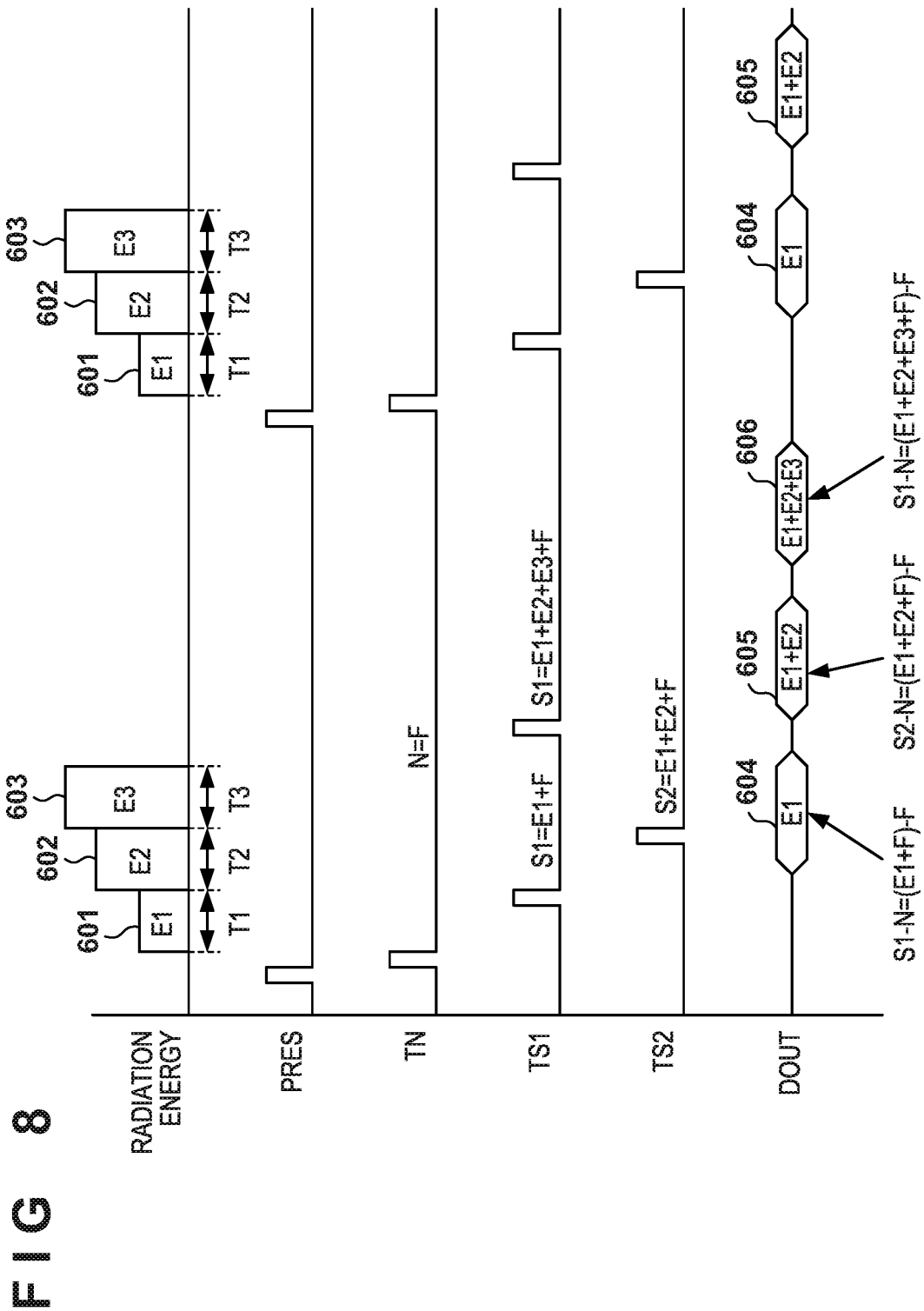
FIG. 8 is a timing chart showing an operation in the fourth mode.

In the fourth to sixth modes, the sample and hold circuits 270, 280, and 290 are used to output radiation images of three or four energies to be separable from each other. FIG. 8 shows the operation of the radiation imaging apparatus 100 or radiation imaging system 1 in the fourth mode. In FIG. 8, the abscissa indicates a time. "Radiation energy" is energy of radiation which is emitted from the radiation source 400 and irradiates the radiation imaging apparatus 100. "PRES" is the reset signal PRES. "TS1" is the sample and hold signal TS1. "TS2" is the sample and hold signal TS2. "DOUT" is an output of the A/D convertor 170. The control apparatus 350 can control synchronization of radiation emission from the radiation source 400 and the operation of the radiation imaging apparatus 100. The timing generator 130 controls an operation in the radiation imaging apparatus 100. The clamp signal PCL is also activated over a predetermined period in a period during which the reset signal PRES is activated, and the clamp circuit 260 clamps a noise level.

The conversion element 210 is reset by activating the reset signal PRES over a predetermined period. Subsequently, radiation 601 having the first energy E1, radiation 602 of the second energy E2, and radiation 603 having third energy E3 are emitted. The first to third energies E1 to E3 can be different from each other. It is only necessary, however, that at least two of them are different from each other. Note that the radiations 601, 602, and 603 may be emitted successively in terms of time or with a time interval between them. In the fourth mode, the conversion element 210 is not reset in a period that includes the first period T1 during which the radiation 601 is emitted, the second period T2 during which the radiation 602 is emitted, and the third period T3 during which the radiation 603 is emitted.

The irradiation times of the radiations 601, 602, and 603 are preset and before irradiation with the radiation 601, the sample and hold signal TN is activated over a predetermined period after the reset signal PRES is activated over the predetermined period. The conversion element 210 is reset by activating the reset signal PRES over the predetermined period. At this time, the clamp signal PCL is also activated over a predetermined period, and the clamp circuit 260 clamps a noise level. Then, the sample and hold circuit 270 can sample and hold the noise level by activating the sample and hold signal TN over a predetermined period. This noise level is indicated as "F" in FIG. 8.

Next, the radiation 601 of the first energy E1 is emitted. Then, a sample and hold operation performed by the sample and hold circuit 280 in accordance with the sample and hold signal TS1 ends immediately before the next irradiation with the radiation 602 of the second energy E2. Note that in accordance with the sample and hold signal TS1, the sample and hold circuit 280 samples and holds a signal (E1+F) which is obtained by adding the signal (E1) generated by irradiation with the radiation 511 having the first energy E1 to the noise level (F) of the clamp circuit 260. The signal (E1+F) sampled and held by the sample and hold circuit 280 in accordance with the sample and hold signal TS1 is output, from the radiation imaging apparatus 100, as the radiation signal 513 corresponding to irradiation with the radiation of the first energy E1. At this time, the amplifier unit 160 performs differential amplification on a radiation signal (S1=E1+F) sampled and held by the sample and hold circuit 280, and a noise level (N=F) sampled and held by the sample and hold circuit 270. Accordingly, radiation signals 604 each corresponding to S1−N=(E1+F)−F=E1 are output from the radiation imaging apparatus 100.

Subsequently to irradiation with the radiation 601 of the first energy E1 in the first period T1, irradiation with the radiation 602 of the second energy E2 is performed in the second period T2. Consequently, in addition to charges generated by irradiation with the radiation 601 of the first energy E1 in the first period T1, charges generated by irradiation with the radiation 602 of the second energy E2 in the second period T2 are accumulated in the charge accumulation portion of the conversion element 210. The clamp circuit 260 outputs a radiation signal corresponding to the charges accumulated in the conversion element 210.

Immediately before the next irradiation with the radiation 603 of the third energy E3, a sample and hold operation performed by the sample and hold circuit 290 in accordance with the sample and hold signal TS2 ends. Note that in accordance with the sample and hold signal TS2, the sample and hold circuit 290 samples and holds a signal (E1+E2+F) which is obtained by adding the signal (E2) generated by irradiation with the radiation 602 having the second energy E2 to the signal corresponding to (E1+F). This sampled and held signal (E1+E2+F) is output, from the radiation imaging apparatus 100, as radiation signals 605 corresponding to irradiation with the radiation 601 of the first energy E1 and the radiation 602 of the second energy E2. At this time, the amplifier unit 160 performs differential amplification on a radiation signal (S2=E1+E2+F) sampled and held by the sample and hold circuit 290, and the noise level (N=F) sampled and held by the sample and hold circuit 270. Accordingly, the radiation signals 605 each corresponding to S2−N=(E1+E2+F)−F=E1+E2 are output from the radiation imaging apparatus 100. Note that a signal via the column signal line 321 can be supplied to one of the differential input pair of the amplifier unit 160, and a signal selected out of signals via the column signal line 322 and column signal line 323 can be supplied to the other of the differential input pair.

Subsequently, after the end of irradiation with the radiation 603 of the third energy E3, the sample and hold circuit 280 performs a sample and hold operation in accordance with the sample and hold signal TS1. Note that in accordance with the sample and hold signal TS1, the sample and hold circuit 280 samples and holds a signal (E1+E2+E3+F) which is obtained by adding the signal (E3) generated by irradiation with the radiation 603 having the third energy E3 to the signal corresponding to (E1+E2+F). This sampled and held signal (E1+E2+E3+F) is output, from the radiation imaging apparatus 100, as a radiation signal 606 corresponding to irradiation with the radiations 601 to 603 of the first to third energies E1 to E3. At this time, the amplifier unit 160 performs differential amplification on a radiation signal (S1=E1+E2+E3+F) sampled and held by the sample and hold circuit 280, and the noise level (N=F) sampled and held by the sample and hold circuit 270. Accordingly, the radiation signal 606 corresponding to S1−N=(E1+E2+E3+F)−F=E1+E2+E3 is output from the radiation imaging apparatus 100.

The signal processor 352 of the control apparatus 350 obtains a subtraction image by processing the radiation signals 604, 605, and 606 in accordance with the energy subtraction method. Note that the signal processor 352 can obtain, by subtracting the value of each radiation signal 605 from the value of the radiation signal 606, a radiation image generated by irradiation with the radiation 603 of the third energy E3. The signal processor 352 can also obtain, by subtracting the value of each radiation signal 604 from the value of a corresponding one of the radiation signals 605, a radiation image generated by irradiation with the radiation 602 of the second energy E2. Thus, the signal processor 352 can obtain the radiation images of the first, second, and third energies E1, E2, and E3. The subtraction image can be obtained by processing these radiation images in accordance with the energy subtraction method.

Figure 9:
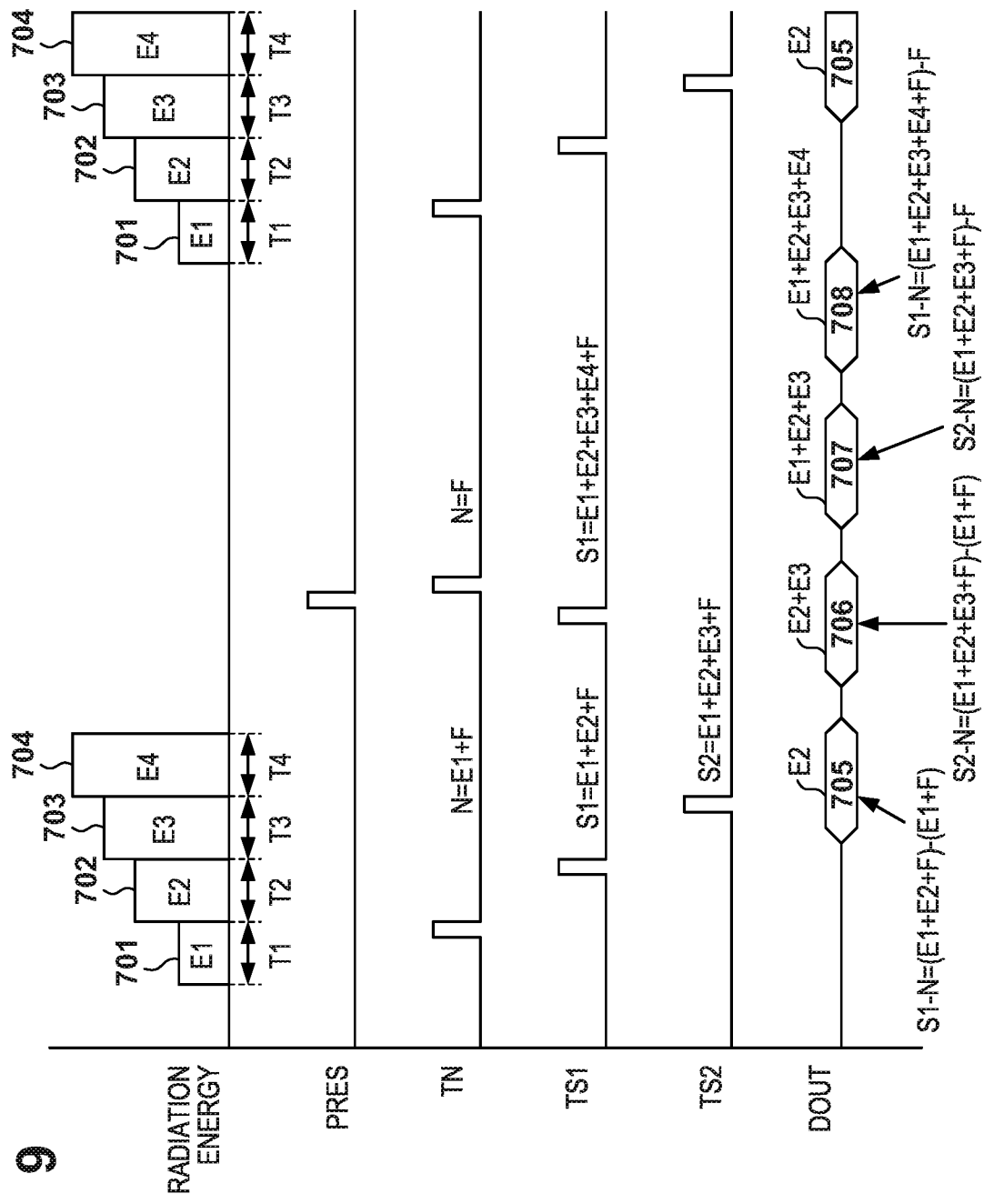
FIG. 9 is a timing chart showing an operation in the fifth mode.

FIG. 9 shows the operation of the radiation imaging apparatus 100 or radiation imaging system 1 in the fifth mode. In FIG. 9, the abscissa indicates a time. "Radiation energy" is energy of radiation which is emitted from the radiation source 400 and irradiates the radiation imaging apparatus 100. "PRES" is the reset signal PRES. "TS1" is the sample and hold signal TS1. "TS2" is the sample and hold signal TS2. "DOUT" is an output of the A/D convertor 170. The control apparatus 350 can control synchronization of radiation emission from the radiation source 400 and the operation of the radiation imaging apparatus 100. The timing generator 130 controls an operation in the radiation imaging apparatus 100. The clamp signal PCL is also activated over a predetermined period in a period during which the reset signal PRES is activated, and the clamp circuit 260 clamps a noise level.

The conversion element 210 is reset by activating the reset signal PRES over a predetermined period. Subsequently, radiation 701 having the first energy E1, radiation 702 having the second energy E2, radiation 703 having the third energy E3, and radiation 704 having fourth energy E4 are emitted. The first to fourth energies E1 to E4 can be different from each other. It is only necessary, however, that at least two of them are different from each other. Note that the radiations 701, 702, 703, and 704 may be emitted successively in terms of time or with a time interval between them. In the fifth mode, the conversion element 210 is not reset in a period that includes the first period T1 during which the radiation 701 is emitted, the second period T2 during which the radiation 702 is emitted, the third period T3 during which the radiation 703 is emitted, and the fourth period T4 during which the radiation 704 is emitted.

The irradiation times of the radiations 701 to 704 are preset and before irradiation with the radiation 701, the reset signal PRES is activated over a predetermined period (not shown). The conversion element 210 is reset by activating the reset signal PRES over the predetermined period.

First, the radiation 701 of the first energy E1 is emitted. Then, a sample and hold operation performed by the sample and hold circuit 270 in accordance with the sample and hold signal TN ends immediately before the next irradiation with the radiation 702 of the second energy E2. Note that in accordance with the sample and hold signal TN, the sample and hold circuit 270 samples and holds the signal (E1+F) which is obtained by adding the signal (E1) generated by irradiation with the radiation 701 having the first energy E1 to the noise level (F) of the clamp circuit 260.

Immediately before the next irradiation with the radiation 702 of the second energy E2, a sample and hold operation performed by the sample and hold circuit 280 in accordance with the sample and hold signal TS1 ends. Note that in accordance with the sample and hold signal TS1, the sample and hold circuit 280 samples and holds the signal (E1+E2+F) which is obtained by adding the signal (E2) generated by irradiation with the radiation 702 having the second energy E2 to the signal corresponding to (E1+F).

Subsequently, the amplifier unit 160 performs differential amplification on a radiation signal (S1=E1+E2+F) sampled and held by the sample and hold circuit 280, and the noise level (N=F) sampled and held by the sample and hold circuit 270. Then, radiation signals 705 each corresponding to S1−N=(E1+E2+F)−(E1+F)=E2 are output from the radiation imaging apparatus 100.

Immediately before the next irradiation with the radiation 703 of the third energy E3, a sample and hold operation performed by the sample and hold circuit 290 in accordance with the sample and hold signal TS2 ends. Note that in accordance with the sample and hold signal TS2, the sample and hold circuit 290 samples and holds the signal (E1+E2+E3+F) which is obtained by adding the signal (E3) generated by irradiation with the radiation 703 having the third energy E3 to the signal corresponding to (E1+E2+F).

Subsequently, the amplifier unit 160 performs differential amplification on the radiation signal (S1=E1+E2+E3+F) sampled and held by the sample and hold circuit 290, and the noise level (N=F) sampled and held by the sample and hold circuit 270. Then, a radiation signal 706 corresponding to S2−N=(E1+E2+E3+F)−(E1+F)=E2+E3 is output from the radiation imaging apparatus 100.

Furthermore, after irradiation with the radiation 704 of the fourth energy E4, the sample and hold circuit 280 performs a sample and hold operation in accordance with the sample and hold signal TS1. Note that in accordance with the sample and hold signal TS1, the sample and hold circuit 280 samples and holds a signal (E1+E2+E3+E4+F) which is obtained by adding the signal (E4) generated by irradiation with the radiation 704 having the fourth energy E4 to the signal corresponding to (E1+E2+E3+F).

Subsequently, the sample and hold signal TN is activated over a predetermined period after the reset signal PRES is activated over the predetermined period. The conversion element 210 is reset by activating the reset signal PRES over the predetermined period. At this time, the clamp signal PCL is also activated over a predetermined period, and the clamp circuit 260 clamps a noise level. Then, the sample and hold circuit 270 can sample and hold the noise level (F) by activating the sample and hold signal TN over a predetermined period.

Subsequently, the amplifier unit 160 performs differential amplification on a radiation signal (S1=E1+E2+E3+E4+F) sampled and held by the sample and hold circuit 280, and the noise level (N=F) sampled and held by the sample and hold circuit 270. Then, the radiation signal 706 corresponding to S1−N=(E1+E2+E3+E4+F)−(E1+F)=E2+E3+E4 is output from the radiation imaging apparatus 100.

Subsequently, the amplifier unit 160 performs differential amplification on the radiation signal (S1=E1+E2+E3+E4+F) sampled and held by the sample and hold circuit 270, and the noise level (N=F) sampled and held by the sample and hold circuit 270. Then, the radiation signal 706 corresponding to S1−N=(E1+E2+E3+E4+F)−(F)=E1+E2+E3+E4 is output from the radiation imaging apparatus 100.

The signal processor 352 of the control apparatus 350 obtains a subtraction image by processing the radiations 701, 702, 703, and 704 in accordance with the energy subtraction method. Note that the signal processor 352 can obtain, by subtracting the value of a radiation signal 707 from the value of a radiation signal 708, a radiation image generated by irradiation with the radiation 704 of the fourth energy E4. The signal processor 352 can also obtain, by subtracting the value of the radiation signal 706 from the value of the radiation signal 707, a radiation image generated by irradiation with the radiation 701 of the first energy E1. The signal processor 352 can further obtain, by subtracting the value of each radiation signal 705 from the value of the radiation signal 706, a radiation image generated by irradiation with the radiation 703 of the third energy E3.

Thus, the signal processor 352 can obtain the radiation images of the first, second, third, and fourth energies E1, E2, E3, and E4. The subtraction image can be obtained by processing these radiation images in accordance with the energy subtraction method.

It is further possible to obtain radiation images of more energies by increasing the number of sample and hold portions.

The second to fifth modes are suitable for a case in which the radiation source 400 capable of changing radiation energy at a high speed is available. The radiation energy can be changed stepwise as in the above-described examples but may be changed successively. The radiation energy can be changed by changing the tube voltage of the radiation source 400. Alternatively, the radiation energy may be changed by emitting radiation having a wide energy band (wavelength band) from a radiation source and switching a plurality of filters.

Figure 10:
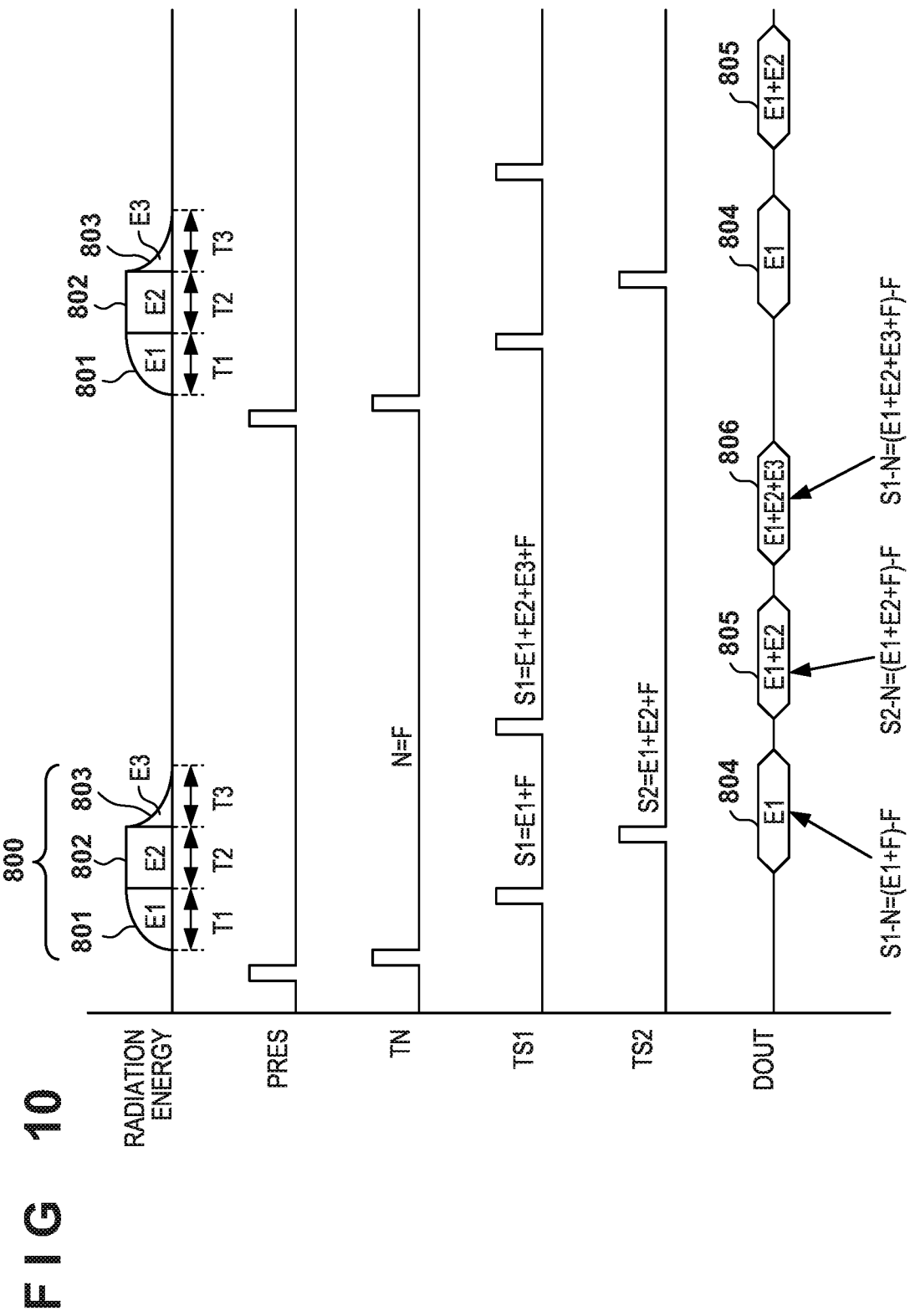
FIG. 10 is a timing chart showing an operation in the sixth mode.

FIG. 10 shows the operation of the radiation imaging apparatus 100 or radiation imaging system 1 in the sixth mode. In FIG. 10, the abscissa indicates a time. "Radiation energy" is energy of radiation which is emitted from the radiation source 400 and irradiates the radiation imaging apparatus 100. "PRES" is the reset signal PRES. "TS1" is the sample and hold signal TS1. "TS2" is the sample and hold signal TS2. "DOUT" is an output of the A/D convertor 170. The control apparatus 350 can control synchronization of radiation emission from the radiation source 400 and the operation of the radiation imaging apparatus 100. The timing generator 130 controls an operation in the radiation imaging apparatus 100. The clamp signal PCL is also activated over a predetermined period in a period during which the reset signal PRES is activated, and the clamp circuit 260 clamps a noise level.

In the sixth mode, the fact that the waveform (waveform change) of the radiation energy generated by the radiation source 400 is not rectangular is used. As exemplified in FIG. 10, rising and falling of radiation may not be rectangular. Note that the waveform that is not rectangular may be formed on purpose. In FIG. 10, the waveform of radiation 800 includes radiations 801, 802, and 803. The average value E1 of the energy of the radiation 801 in the period T1, the average value E2 of the energy of the radiation 802 in the period T2, and the average value E3 of the energy of the radiation in the period T3 are different from each other. The energy subtraction method can be implemented by using this.

Before irradiation with the radiation 800, the reset signal PRES is activated over a predetermined period, and then the sample and hold signal TN is activated over a predetermined period. The conversion element 210 is reset by activating the reset signal PRES over the predetermined period. At this time, the clamp signal PCL is also activated over a predetermined period, and the clamp circuit 260 clamps a noise level. Then, the sample and hold circuit 270 can sample and hold the noise level by activating the sample and hold signal TN over the predetermined period.

Then, irradiation with the radiation 800 is started. Immediately before the period T2, a sample and hold operation performed by the sample and hold circuit 280 in accordance with the sample and hold signal TS1 ends. Note that in accordance with the sample and hold signal TS1, the sample and hold circuit 280 samples and holds the signal (E1+F) which is obtained by adding the signal (E1) generated by irradiation with the radiation 511 having the first energy E1 to the noise level (F) of the clamp circuit 260. The signal (E1+F) sampled and held by the sample and hold circuit 280 in accordance with the sample and hold signal TS1 is output, from the radiation imaging apparatus 100, as radiation signals 804 corresponding to irradiation with the radiation of the first energy E1. At this time, the amplifier unit 160 performs differential amplification on a radiation signal (S1=E1+F) sampled and held by the sample and hold circuit 280, and the noise level (N=F) sampled and held by the sample and hold circuit 270. Accordingly, the radiation signals 804 each corresponding to S1−N=(E1+F)−F=E1 are output from the radiation imaging apparatus 100.

In the period T2, in addition to charges generated by irradiation with the radiation 801 of the first energy E1 in the first period T1, charges generated by irradiation with the radiation 802 of the second energy E2 in the second period T2 are accumulated in the charge accumulation portion of the conversion element 210. The clamp circuit 260 outputs a radiation signal according to the charges accumulated in the conversion element 210.

Immediately before the period T3, a sample and hold operation performed by the sample and hold circuit 290 in accordance with the sample and hold signal TS2 ends. Note that in accordance with the sample and hold signal TS2, the sample and hold circuit 290 samples and holds the signal (E1+E2+F) which is obtained by adding the signal (E2) generated by irradiation with the radiation 802 having the second energy E2 to the signal corresponding to (E1+F). This signal (E1+E2+F) is output, from the radiation imaging apparatus 100, as radiation signals 805 corresponding to the radiation 801 of the first energy E1 and the radiation 802 of the second energy E2. At this time, the amplifier unit 160 performs differential amplification on the radiation signal (S2=E1+E2+F) sampled and held by the sample and hold circuit 290, and the noise level (N=F) sampled and held by the sample and hold circuit 270. Accordingly, the radiation signals 805 each corresponding to S2−N=(E1+E2+F)−F=E1+E2 are output from the radiation imaging apparatus 100.

Subsequently, the sample and hold circuit 280 performs a sample and hold operation in accordance with the sample and hold signal TS1 after the end of the period T3 and the end of the radiation signals 804. Note that in accordance with the sample and hold signal TS1, the sample and hold circuit 280 samples and holds the signal (E1+E2+E3+F) which is obtained by adding the signal (E3) generated by irradiation with the radiation 803 having the third energy E3 to the signal corresponding to (E1+E2+F). This sampled and held signal (E1+E2+E3+F) is output, from the radiation imaging apparatus 100, as a radiation signal 806 corresponding to irradiation with the radiations 801 to 803 of the first to third energies E1 to E3. At this time, the amplifier unit 160 performs differential amplification on the radiation signal (S1=E1+E2+E3+F) sampled and held by the sample and hold circuit 280, and the noise level (N=F) sampled and held by the sample and hold circuit 270. Accordingly, the radiation signal 806 corresponding to S1−N=(E1+E2+E3+F)−F=E1+E2+E3 is output from the radiation imaging apparatus 100.

The signal processor 352 of the control apparatus 350 obtains a subtraction image by processing the radiation signals 804, 805, and 806 in accordance with the energy subtraction method. Note that the signal processor 352 can obtain, by subtracting the value of each radiation signal 805 from the value of the radiation signal 806, a radiation image generated by irradiation with the radiation 803 of the third energy E3. The signal processor 352 can also obtain, by subtracting the value of each radiation signal 804 from the value of a corresponding one of the radiation signals 805, a radiation image generated by irradiation with the radiation 802 of the second energy E2. Thus, the signal processor 352 can obtain the radiation images of the first, second, and third energies E1, E2, and E3. The signal processor 352 can obtain the subtraction image by processing these radiation images in accordance with the energy subtraction method.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-219952, filed Nov. 10, 2016, which is hereby incorporated by reference herein in its entirety.

What is claimed is:

1. A radiation imaging apparatus that obtains a radiation image by an energy subtraction method of obtaining a new image by processing a plurality of images obtained by capturing an object a plurality of times while changing energy of radiation to irradiate the object, the apparatus comprising:

a pixel array in which a plurality of pixels are arrayed to form a plurality of rows and a plurality of columns;

each of the plurality of pixels including a conversion element having a charge accumulation portion configured to accumulate charges generated in accordance with radiation, a source follower circuit having a gate forming, with the charge accumulation portion, a charge-voltage convertor that converts the charges accumulated in the charge accumulation portion into a voltage, a sample-and-hold circuit configured to sample-and-hold a signal associated with the converted voltage without changing the potential of the charge-voltage convertor, a reset portion that resets a potential of the charge-voltage convertor including the gate and the charge accumulation portion, and at least one transistor having a first main electrode which is connected to the charge accumulation portion, a second main electrode which is not connected to the charge accumulation portion, and a control electrode;

each of the plurality of pixels being configured to perform an operation of outputting, via the sample-and-hold circuit without changing the potential of the charge-voltage convertor, a first signal corresponding to charges generated by the conversion element in a first period which starts after resetting the potential of the charge-voltage convertor by the reset portion, and an operation of outputting, via the sample-and-hold circuit without changing the potential of the charge-voltage convertor, a second signal corresponding to charges generated by the conversion element in the first period and a second period after the first period, wherein radiation having first energy is emitted in the first period, and radiation having second energy is emitted in the second period, and the radiation imaging apparatus has a mode in which, in each of the plurality of pixels, the reset portion does not reset the potential of the charge-voltage converter and a voltage applied to the control electrode of the at least one transistor does not change so as not to change the potential of the charge-voltage convertor during a period that includes the first period and the second period.

2. The apparatus according to claim 1, wherein the sample-and-hold circuit includes a switch and a capacitor, and is configured to write the signal associated with the converted voltage in the capacitor via the switch when the switch turns on, and the at least one transistor electrically connects the first main electrode and the second main electrode by receiving an ON voltage at the control electrode.

3. The apparatus according to claim 1, wherein the reset portion includes a reset transistor having a third main electrode which is connected to the charge accumulation portion of the charge-voltage convertor, a fourth main electrode which is connected to a reset potential, and a second control electrode, and the reset transistor electrically connects the third main electrode and the fourth main electrode by receiving an ON voltage at the second control electrode, and in the mode, a voltage applied to the second control electrode of the reset transistor does not change whereby the potential of the charge-voltage convertor does not change during the period that includes the first period and the second period.

4. The apparatus according to claim 1, wherein a plurality of imaging operations are performed, each of the plurality of operations including the operation of outputting the first signal in the first period, and the operation of outputting the second signal in the first period and the second period, and the first period of each of the plurality of imaging operations starts after the charge-voltage convertor of each of the plurality of pixels is reset by the reset portion thereof.

5. The apparatus according to claim 1, wherein the sample-and-hold circuit includes a first signal sample-and-hold circuit that sample-and-holds the first signal and a second signal sample-and-hold circuit that sample-and-holds the second signal, and each of the plurality of pixels outputs the first signal via the first signal sample-and-hold circuit, and outputs the second signal via the second signal sample-and-hold circuit.

6. The apparatus according to claim 1, wherein each of the plurality of pixels includes a plurality of sample-and-hold circuits which includes the sample-and-hold circuit, and each of the plurality of pixels outputs the first signal and the second signal via one of the plurality of sample-and-hold circuits.

7. The apparatus according to claim 1, wherein the sample-and-hold circuit includes a first signal sample-and-hold circuit that sample-and-holds a signal corresponding to charges generated by the conversion element, and a second signal sample-and-hold circuit that sample-and-holds a signal corresponding to a noise level, and the radiation imaging apparatus further comprises (i) a readout circuit that reads out, from each of the plurality of pixels, a first signal held by the first signal sample-and-hold circuit, and a second signal held by the second signal sample-and-hold circuit, and (ii) an amplifier unit that amplifies a difference between the first signal and the second signal read out by the readout circuit.

8. The apparatus according to claim 1, wherein each of the plurality of pixels further performs, in a third period different from the first period and the second period, an operation of outputting third signals corresponding to charges generated by the conversion element in the first period and the second period, radiation having third energy is emitted in the third period, and in each of the plurality of pixels, the reset portion does not rest the charge-voltage converter in a period that includes the first period, the second period, and the third period.

9. The apparatus according to claim 8, wherein the sample-and-hold circuit includes a plurality of signal sample-and-hold circuits that sample-and-hold signals corresponding to charges generated by the conversion element, and each of the plurality of pixels outputs the first signal, the second signal, and the third signal via one of the pluralities of signal sample-and-hold circuits.

10. The apparatus according to claim 8, wherein the sample-and-hold circuit includes a plurality of first signal sample-and-bold circuits that sample-and-hold signals corresponding to charges generated by the conversion element, and a second signal sample-and-hold circuit that sample-and-holds a signal corresponding to charges generated by the conversion element, and the radiation imaging apparatus further comprises (i) a readout circuit that reads out, from each of the plurality of pixels, a first signal which is held by the first signal sample-and-hold circuit selected out of the plurality of first signal sample-and-hold circuits and a second signal which is held by the second signal sample-and-hold circuit, and (ii) an amplifier unit that amplifies a difference between the first signal and the second signal read out by the readout circuit.

11. The apparatus according to claim 1, further comprising a signal processor that generates a radiation image by the energy subtraction method based on the first signal and the second signal.

12. A radiation imaging system comprising:
the radiation imaging apparatus defined in claim 1; and
a control apparatus that controls a radiation source and the radiation imaging apparatus.

13. A radiation imaging system that obtains a radiation image by an energy subtraction method of obtaining a new image by processing a plurality of images obtained by capturing an object a plurality of times while changing energy of radiation to irradiate the object, the system comprising:
- a pixel array in which a plurality of pixels are arrayed to form a plurality of rows and a plurality of columns;
- a signal processor that processes a signal output from the pixel array;
- each of the plurality of pixels including a conversion element having a charge accumulation portion configured to accumulate charges generated in accordance with radiation, a source follower circuit having a gate forming, with the charge accumulation portion, a charge-voltage convertor that converts the charges accumulated in the charge accumulation portion into a voltage, a sample-and-hold circuit configured to sample-and-hold a signal associated with the converted voltage without changing the potential of the charge-voltage convertor, and a reset portion that resets a potential of the charge-voltage convertor including the gate and the charge accumulation portion, and at least one transistor having a first main electrode which is connected to the charge accumulation portion, a second main electrode which is not connected to the charge accumulation portion, and a control electrode; and
- each of the plurality of pixels being configured to perform an operation of outputting, via the sample-and-hold circuit without changing the potential of the charge-voltage convertor, a first signal corresponding to charges generated by the conversion element in a first period which starts after resetting the potential of the charge-voltage convertor by the reset portion, and an operation of outputting, via the sample-and-hold circuit without changing the potential of the charge-voltage convertor, a second signal corresponding to charges generated by the conversion element in the first period and a second period after the first period, wherein
- radiation having first energy is emitted in the first period, and radiation having second energy is emitted in the second period,
- the radiation imaging system has a mode in which, in each of the plurality of pixels, the reset portion does not reset the potential of the charge-voltage converter and a voltage applied to the control electrode of the at least one transistor does not change so as not to change the potential of the charge-voltage convertor during a period that includes the first period and the second period, and
- the signal processor generates a radiation image by the energy subtraction method based on the first signal and the second signal.

14. The system according to claim 13, wherein the at least one transistor electrically connects the first main electrode and the second main electrode by receiving an ON voltage at the control electrode.

15. The system according to claim 13, further comprising a controller that controls a radiation source to send a command to emit the radiation having the first energy in the first period and emit the radiation having the second energy in the second period.

16. The system according to claim 13, further comprising a controller that controls the pixel array such that a period during which radiation emitted from a radiation source has the first energy becomes the first period, and a period during which radiation emitted from the radiation source has the second energy becomes the second period.

17. A radiation imaging method of obtaining a radiation image by an energy subtraction method using a radiation imaging apparatus, the energy subtraction method being a method of obtaining a new image by processing a plurality of images obtained by capturing an object plurality of times while changing energy of radiation to irradiate the object, the radiation imaging apparatus comprising a pixel array in which a plurality of pixels are arrayed to form a plurality of rows and a plurality of columns, each of the plurality of pixels including a conversion element having a charge accumulation portion configured to accumulate charges generated in accordance with radiation, a source follower circuit having a gate forming, with the charge accumulation portion, a charge-voltage convertor that converts the charges accumulated in the charge accumulation portion into a voltage, a sample-and-hold circuit configured to sample-and-hold a signal associated with the converted voltage without changing the potential of the charge-voltage convertor, a reset portion that resets a potential of the conversion element including the gate and the charge accumulation portion, and at least one transistor having a first main electrode which is connected to the charge accumulation portion, a second main electrode which is not connected to the charge accumulation portion, and a control electrode, the method comprising:
- causing each of the plurality of pixels to perform an operation of outputting, via the sample-and-hold circuit without changing the potential of the charge-voltage convertor, a first signal corresponding to charges generated by the conversion element in a first period which starts after resetting of the charge-voltage convertor by the reset portion, and an operation of outputting, via the sample-and-hold circuit without changing the potential of the charge-voltage convertor, a second signal corresponding to charges generated by the conversion element in the first period and a second period after the first period, and
- obtaining a radiation image based on a signal corresponding to the first signal and a signal corresponding to the second signal, wherein
- radiation laying first energy is emitted in the first period, and radiation having second energy is emitted in the second period, and
- in the causing and the obtaining, in each of the plurality of pixels, the reset portion does not reset the potential of the charge-voltage converter and a voltage applied to the control electrode of the at least one transistor does not change so as to not change the potential of the charge-voltage convertor during a period that includes the first period and the second period.

18. The method according to claim 17, wherein the at least one transistor electrically connects the first main electrode and the second main electrode by receiving an ON voltage at the control electrode.

* * * * *